(12) United States Patent
Wu

(10) Patent No.: US 8,974,818 B2
(45) Date of Patent: Mar. 10, 2015

(54) CUSTOM-FORMULATED PHOSPHOLIPID MICROBUBBLES AND METHODS AND USES THEREOF

(76) Inventor: Henry Wu, New York, NY (US)

(*) Notice: Subject to any disclaimer, the term of this patent is extended or adjusted under 35 U.S.C. 154(b) by 575 days.

(21) Appl. No.: 13/010,601

(22) Filed: Jan. 20, 2011

(65) Prior Publication Data

US 2011/0177159 A1 Jul. 21, 2011

Related U.S. Application Data

(60) Provisional application No. 61/296,767, filed on Jan. 20, 2010.

(51) Int. Cl.
*A61K 9/127* (2006.01)
*A61K 31/20* (2006.01)
*A61K 9/00* (2006.01)
*A61K 9/107* (2006.01)

(52) U.S. Cl.
CPC ............ *A61K 31/20* (2013.01); *A61K 9/0019* (2013.01); *A61K 9/1075* (2013.01); *A61K 9/127* (2013.01)
USPC .......................................................... 424/450

(58) Field of Classification Search
USPC .......................................................... 424/450
See application file for complete search history.

(56) References Cited

U.S. PATENT DOCUMENTS

| | | | |
|---|---|---|---|
| 5,434,183 A * | 7/1995 | Larsson-Backstrom | 514/549 |
| 5,558,092 A | 9/1996 | Unger et al. | |
| 5,580,575 A * | 12/1996 | Unger et al. | 424/450 |
| 2001/0044583 A1* | 11/2001 | Unger et al. | 600/458 |
| 2004/0052837 A1* | 3/2004 | Stillwell et al. | 424/450 |
| 2006/0241080 A1 | 10/2006 | Dror et al. | |
| 2007/0081946 A1 | 4/2007 | Schneider et al. | |
| 2008/0096961 A1 | 4/2008 | Serhan et al. | |
| 2008/0138393 A1* | 6/2008 | Leverett et al. | 424/450 |
| 2008/0206316 A1* | 8/2008 | Barrow et al. | 424/450 |
| 2008/0279925 A1* | 11/2008 | Allam et al. | 424/450 |
| 2009/0285882 A1* | 11/2009 | Weiss et al. | 424/450 |
| 2011/0160161 A1* | 6/2011 | Sampalis et al. | 514/78 |

OTHER PUBLICATIONS

Trosko, J.E., et al in Mutation Research, 480-481, pp. 219-229. 2001.*
Marchioli, R., Circulation, vol. 105, p. 1897, 2002.*
Hu et al, Jama, vol. 287, pp. 1815-1821, 2002.*
van Oss, Carel J; "Nature of Specific Ligand—Receptor Bonds, in Particular the Antigen-Antibody Bond"; Journal of Immunoassay, vol. 21 (2 & 3), May-Aug. 2000; pp. 109-142.
Grimminger, F. et al; "Omega-3 Lipid Infusion in a Heart Allotransplant Model: Shift in Fatty Acid and Lipid Mediator Profiles and Prolongation of Transplant Survival"; Circulation 1996, vol. 93(2), pp. 365-371.

(Continued)

*Primary Examiner* — Gollamudi Kishore
(74) *Attorney, Agent, or Firm* — Dickstein Shapiro LLP

(57) ABSTRACT

A phospholipid microbubble comprising a shell which comprises a plurality of polyunsaturated fatty acid ("PUFA")-containing phospholipids, and a core of inert gas surrounded by the shell comprising the plurality of PUFA-containing phospholipids. The present invention also provides methods of delivering a prophylactically or therapeutically effective amount of PUFA to an area of disease or injury in a subject. The present invention also provides methods of preventing or treating a disease in a subject using a prophylactically or therapeutically effective amount of the aforementioned phospholipid microbubbles.

4 Claims, 2 Drawing Sheets

(56) References Cited

OTHER PUBLICATIONS

Bekeredjian, Raffi et al.; "Use of Ultrasound Contrast Agents for Gene or Drug Delivery in Cardiovascular Medicine"; Journal of the American College of Cardiology, vol. 45, No. 3, Feb. 1, 2005, pp. 329-335.

Billman, George E. et al; "Prevention of ischemica-induced ventricular fibrillation by ω3 fatty acids"; Proc. Natl. Acad. Sci, USA, vol. 91, May 1994, pp. 4427-4430.

"Dietary supplementation with n-3 polyunsaturated fatty acids and vitamin E after myocardial infarction; results of the GISSI-Prevenzione trial"; The Lancet, vol. 354, Aug. 7, 1999, pp. 447-455.

Feinstein, Steven B.; "The powerful microbubble: from bench to bedside, from intravascular indicator to therapeutic delivery system, and beyond"; Am J Physiol Heart Circ Physiol 287: H450-H457, Aug. 2004.

Gardai, Shyra J. et al.; "Recognition ligands on apoptotic cells: a perspective"; Journal of Leukocyte Biology, vol. 79, May 2006, pp. 896-903.

Huang, Shao-Ling et al.; "A Method to Co-Encapsulate Gas and Drugs in Liposomes for Ultrasound-Controlled Drug Delivery"; Ultrasound in Medicine & Biology, vol. 34, No. 8, pp. 1272-1280, (2008).

Jacobson, Terry, A.; "Secondary Prevention of Coronary Artery Disease with Omega-3 Fatty Acids"; The American Journal of Cardiology (www.AJConline.org), vol. 98 (4A), Aug. 21, 2006, pp. 62i-70i.

Jung, Un Ju et al.; "n-3 Fatty acids and cardiovascular disease: mechanisms underlying beneficial effects [1-4]"; Am J Clin Nutr 2008, 87(suppl): 2003S-2009S.

Lindner, Jonathan R. et al; "Noninvasive Imaging of Inflammation by Ultrasound Detection of Phagocytosed Microbubbles"; Circulation 2000; 102; pp. 531-538.

Lindner, Jonathan, R. et a; "Noninvasive Ultrasound Imaging of Inflammation Using Microbubbles Targeted to Activated Leukocytes;"Circulation 2000; 102; pp. 2745-2750.

Lionetti, Vincenzo et al; "Enhanced Caveolae-Mediated Endocytosis by Diagnostic Ultrasound In Vitro"; Ultrasound in Medicine and Biology, vol. 35, No. 1, pp. 136-143, Nov. 1, 2009.

Liu, Yiyao et al.; "Encapsulated ultrasound microbubbles: Therapeutic application in drug/gene delivery"; Journal of Controlled Release 114 (2006), pp. 89-99.

Main, Michael L et al; "Ultrasound contrast agents: balancing safety versus efficacy"; Expert Opin. Drug Saf. (2009) *8 (1), pp. 49-56.

McGuinness, J. et al; "Myocardial protection using an omega-3 fatty acid infusion: Qualification and mechanism of action;"The Journal of Thoracic and Cardiovascular Surgery; vol. 132, No. 1, Jul. 2006, pp. 72-79.

Musiek, Erik S. et al.; "Electrophilic Cyclopentenone Neuroprostanes Are Anti-inflammatory Mediators Formed from the Peroxidation of the ω-3 Polyunsaturated Fatty Acid Docosahexaenoic Acid"; Journal of Biological Chemistry, vol. 283, No. 29, pp. 19927-19935, Jul. 18, 2008.

Pan, Dipanjan, et al.; "Nanomedicine: Perspective and promises with ligand-directed molecular imaging"; European Journal of Radiology 70 (2009) pp. 274-285.

Pound, Eric, M. et al.; "Partitioning of polyunsaturated fatty acids, which prevent cardiac arrhythmias, into phospholipid cell membranes"; Journal of Lipid Research, vol. 42, 2001, pp. 346-351.

Robinson, Jennifer G. et al.; "Antiatherosclerotic and Antithrombotic Effects of Omega-3 Fatty Acids"; The American Journal of Cardiology, vol. 98 (4A), Aug. 21, 2006, pp. 39i-49i.

Schrepf, Rainer, et al.; "Immediate effects of n-3 fatty acid infusion on the induction of sustained ventricular tachycardia"; The Lancet, vol. 363, May 1, 2004, pp. 1441-1442.

Serhan, Charles N. et al.; Resolving inflammation: dual anti-inflammatory and pro-resolution lipid mediators; Nature Reviews: Immunology, vol. 8, May 2008, pp. 349-361.

Simopoulos, A.P.; "The importance of the ratio of omega-6/omega-3 essential fatty acids"; Biomed Pharmacother 56 (2002), pp. 365-379.

Simopoulos, Artemis P.; "Omega-3 Fatty Acids in Inflammation and Autoimmune Diseases"; Journal of the American College of Nutrition, vol. 21, No. 6, pp. 495-505 (2002).

Thies, Frank et al.; "Association of n-3 polyunsaturated fatty acids with stability of atherosclerotic plaques: a randomised controlled trial"; The Lancet, vol. 361, Feb. 8, 2003, pp. 477-485.

Villanueva, Flordeliza S. et al.; "Albumin Microbubble Adherence to Human Coronary Endothelium: Implications for Assessment of Endothelial Function Using Myocardial Contrast Echocardiography"; JACC vol. 30, No. 3, Sep. 1997, pp. 689-693.

Weylandt, Karsten H. et al.; "Polyunsaturated Fatty Acids Exert Antiarrhythmic Actions as Free Acids Rather Than in Phospholipids"; Lipids, vol. 31, No. 9 (1996), pp. 977-982.

Yanagisawa, Kyosuke et al.; "Phagocytosis of Ultrasound Contrast Agent Microbubbles by Kupffer Cells"; Ultrasound in Med. & Biol., vol. 33, No. 2, pp. 318-325, 2007.

Jun. 2, 2011 Notification of Transmittal of The International Search Report and The Written Opinion of the International Searching Authority, or the Declaration for International Application No. PCT/US11/21915.

* cited by examiner

CUSTOM-FORMULATED PHOSPHOLIPID MICROBUBBLES AND METHODS AND USES THEREOF

CROSS-REFERENCE TO RELATED APPLICATIONS

This application claims benefit under 35 U.S.C. §119(e) to U.S. Provisional Patent Application No. 61/296,767, filed Jan. 20, 2010, which is incorporated by reference in its entirety herein.

Throughout this application, several patents, patent applications and references are referenced herein. Disclosures of these patents, patent applications and references in their entirety are hereby incorporated by reference into this application.

BACKGROUND OF THE INVENTION

The present invention generally relates to new pharmacological formulations of phospholipid microbubbles comprising a plurality of phospholipids that allow for the rapid, efficient and target delivery of polyunsaturated fatty acids ("PUFA") to areas of disease or injury in a subject for diagnostic, prophylactic and/or therapeutic aims.

Omega-3 PUFA:

Omega-3 PUFA is an essential nutrient critical for the maintenance of human health. Interest in omega-3 PUFA stems from the first observations by Bang and Dyerberg during the 1970s that death from coronary artery disease (CAD) is extremely rare among the Greenland Eskimos who consume a diet rich in EPA and DHA. Since that seminal discovery, intense basic and animal research has revealed a multitude of beneficial effects of omega-3 PUFA. These positive effects include anti-inflammatory, anti-cancerous, immunomodulatory, anti-diabetic, anti-thrombotic and anti-arrhythmic properties, to name but a few. In addition, numerous epidemiological studies and randomized controlled trials have been conducted that demonstrated similar wide-ranging health benefits in humans. For example, the landmark GISSI-P (Gruppo Italiano per lo Studio della Streptochinasi nell'Infarto Miocardico-Prevenzione) prevention study randomized 11,324 patients with pre-existing CAD to 850 mg of omega-3 PUFA resulted in a 45% reduction in sudden cardiac death and 30% reduction in cardiovascular death. (Dietary supplementation with n-3 polyunsaturated fatty acids and vitamin E after myocardial infarction: results of the GISSI-Prevenzione trial. The Lancet, 1999; 354:447-55). Moreover, the benefits of these essential nutrients appear not to be limited solely to the cardiovascular system but extend to virtually every organ system in the human body. (Simopoulos A P. Omega-3 fatty acids in inflammation and autoimmune diseases. J Am Coll Nutr 2002; 21:495-505).

Tragically, the dietary practices of modern industrial society over the last century have been moving towards a diet that is severely deficient in omega-3 PUFA. This nutritional deficit is further compounded by the rise in the consumption of "processed" foods containing hydrogenated trans-fatty acids and omega-6 PUFA that possess antagonistic properties to omega-3 PUFA. Moreover, the content of omega-3 PUFA in meat products was decreased by the modern practice of raising animals fed with corn-base stock in feedlots rather than grass fed on the open field. Together, these changes resulted in a striking imbalance of pro-inflammatory and anti-inflammatory types of PUFA in the typical modern diet. Up until only recently, humans evolved and flourished on a diet with a ratio of omega-6:omega-3 fatty acids close to 1:1. It has been estimated that today this ratio has risen dramatically to as high as 20:1. (Simopoulos A P. The importance of the ratio of omega-6/omega-3 essential fatty acids. Biomed Pharmacother 2002; 56:365-79). As a consequence of these changes in eating habits, food processing and in agriculture, entire populations are now at risk of developing a wide spectrum of inflammatory, autoimmune and degenerative diseases.

Despite their wide ranging health benefits, the therapeutic use of omega-3 PUFA is currently limited by the lack of a rapid and effective means of delivery. Oral supplementation of omega-3 PUFA requires weeks to months to attain adequate blood levels and to be incorporated into cellular membranes to exert their effects. Furthermore, the "fishy" unpleasant taste of omega-3 PUFA makes it difficult for patients to maintain strict compliance. More importantly, the delayed onset of action of oral supplementation has precluded their use in the treatment of acute emergent medical conditions such as acute myocardial infarction and cerebral vascular accidents and their complications. To achieve a more rapid onset of action, intravenous infusion of omega-3 PUFA has been used successfully to terminate and prevent life-threatening ventricular arrhythmias that occurred in the setting of AMI in various animal models and in humans. (McGuinness J, Neilan T G, Sharkasi A, Bouchier-Hayes D, Redmond J M. Myocardial protection using an omega-3 fatty acid infusion: Quantification and mechanism of action. J Thorn Cardiovasc Surg 2006; 132:72-9; Billman G E, Hallaq H, Leaf A. Prevention of Ischemia-Induced Ventricular Fibrillation by {omega}3 Fatty Acids. PNAS 1994; 91:4427-30; and Schrepf R, Limmert T, Claus Weber P, Theisen K, Sellmayer A. Immediate effects of n-3 fatty acid infusion on the induction of sustained ventricular tachycardia. Lancet 2004; 363:1441-2). Omega-3 PUFA have also been shown to be exert immunomodulatory activity in preventing heart transplant rejection in rats. (Grimminger F, Grimm H, Fuhrer D, et al. {omega}-3 Lipid Infusion in a Heart Allotransplant Model: Shift in Fatty Acid and Lipid Mediator Profiles and Prolongation of Transplant Survival. Circulation 1996; 93:365-71). However, omega-3 PUFA administered by the intravenous route have to be in the form of triglycerides rather than in their free bioactive non-esterified forms. Enzymatic hydrolysis of these triglycerides by endogenous lipases is needed for their release and activation. Because of interindividual differences in the rate of their metabolism, the blood levels of omega-3 PUFA after intravenous infusion were found to be highly variable. (Schrepf R, Limmert T, Claus Weber P, Theisen K, Sellmayer A. Immediate effects of n-3 fatty acid infusion on the induction of sustained ventricular tachycardia. Lancet 2004; 363: 1441-2). Because of the slow and variable rate of hydrolysis and the need to saturate the entire body, a prolonged infusion that lasts an excess of 90 minutes is generally required to ensure that adequate therapeutic levels can be achieved. This unpredictable bioavailability prevents their use in emergent clinical situations such as heart attacks, strokes and their arrhythmic sequela.

Ultrasound Microbubbles:

Prior art ultrasound microbubbles are gas-filled vesicles having diameters on the order of less than 10 microns enclosed in a biocompatible shell composed of a lipid, protein or polymer. The gas core is made of an inert high-molecular weight gas (i.e, perfluorocarbons, sulfur hexafluoride) such as to typically minimize volume loss and to ensure stability. The small size of the microbubbles allow for their unimpeded passage through the microcirculation of the lungs to any organs of the body by intravenous administration. Various formulations of these microbubbles are currently employed as contrast agents to enhance diagnostic images obtained by ultrasonography, as in echocardiography to help visualize the left ventricular cavity of the heart and to assess myocardial perfusion.

More recently, these microbubbles have been modified for therapeutic use as vehicles for drug delivery and for gene therapy. (Feinstein S B. The powerful microbubble: from bench to bedside, from intravascular indicator to therapeutic delivery system, and beyond. Am J Physiol Heart Circ Physiol 2004; 287:H450-7). The dual versatility of microbubbles for molecular imaging and target drug delivery termed "theranostic" applications is only now beginning to be exploited. (Pan D, Lanza G M, Wickline S A, Caruthers S D. Nanomedicine: Perspective and promises with ligand-directed molecular imaging. European Journal of Radiology 2009; 70:274-85). By focusing the ultrasound energy at a desired target site, higher local concentrations of a therapeutic agent may be achieved. For example, U.S. Pat. No. 5,558,092 describes compositions, methods and apparatus for carrying out diagnostic and therapeutic ultrasound. Contrast materials loaded with a therapeutic agent are imaged using diagnostic ultrasound waves, and once seen accumulating in a desired area, are ruptured using ultrasonic waves to generate enhanced cavitation or the targeted release of an agent into the region. Coupling diagnostic and therapeutic ultrasound modes provides additional advantages of monitoring efficacy and dose adjustments. However, the major limiting aspect of the current art remains poor efficiency of delivery.

SUMMARY OF THE INVENTION

In consideration of the above problems, in an aspect of the present invention, a phospholipid microbubble comprising a shell which comprises a plurality of polyunsaturated fatty acid ("PUFA")-containing phospholipids, and a core of inert gas surrounded by the shell comprising the plurality of PUFA-containing phospholipids.

Each of the phospholipids within the shell comprises a polar head group, and two non-polar fatty acid tails, the two non-polar fatty acid tails are linked to the polar head group via a glycerol linkage. The phospholipids can be customized to identify and/or treat a specific disease or injury by selecting a type of polar head groups and/or non-polar fatty acid tails. By way of example, the phospholipid microbubbles can be made of PS polar head groups linked to non-polar fatty acid tails of omega-3 PUFAs (such as EPA, DHA, or a combination thereof) to treat acute myocardial infarction and prevent its arrhythmic complications. Examples of polar head groups that can be used to customize the phospholipids are phosphatidylserine ("PS"), phosphadtidylcholine ("PC"), phosphatidyl-ethanolamine ("PE"), phosphatidylinositol ("PI"), or a combination thereof, in varying proportions depending on the specific diagnostic, prophylactic and/or therapeutic aims. Examples of non-polar fatty acid tails that can be used to customize the phospholipids are omega-3 PUFA (e.g., eicosapentaenoic acid ("EPA"), docosahexaenoic acid ("DHA")), omega-3 PUFA precursors (e.g., α-linolenic acids), omega-3 PUFA-derived metabolites (e.g., resolvins, neuroprotectins, lipoxins, neuroprostanes), omega-6 PUFA, omega-9 PUFA, conjugated linoleic acids, conjugated linoleic acid isomers, or a combination thereof, in varying proportions depending on the specific diagnostic, prophylactic and/or therapeutic aims.

In another aspect, the plurality of PUFA-containing phospholipids comprises a plurality of polar head groups, the plurality of polar head groups comprising phosphatidylserine ("PS"), phosphadtidylcholine ("PC"), phosphatidyl-ethanolamine ("PE"), phosphatidylinositol ("PI"), or a combination thereof.

In another aspect, the plurality of PUFA-containing phospholipids comprises a plurality of non-polar fatty acid tails, the plurality of non-polar fatty acid tails comprising an omega-3 PUFA, an omega-3 PUFA precursor, an omega-3 PUFA-derived metabolite, an omega-6 PUFA, an omega-9 PUFA, a conjugated linoleic acid, a conjugated linoleic acid isomer, or a combination thereof.

In another aspect, the omega-3 PUFA is selected from eicosapentaenoic acid ("EPA"), docosahexaenoic acid ("DHA"), or a combination thereof.

In another aspect, the omega-3 PUFA precursor is an α-linolenic acid.

In another aspect, the omega-3 PUFA-derived metabolite is selected from a resolvin, a neuroprotectin, a lipoxin, a neuroprostane, or a combination thereof.

In another aspect, the inert gas is selected from a perfluorocarbon compound, xenon, hyperpolarized xenon, or other suitable gas that enhances target delivery and/or permits detection and monitoring by MRI. The inert gas can be, preferably, a paramagnetic gas.

In another aspect, the phospholipid microbubble in a micellar form or a liposomal form.

In another aspect, the plurality of PUFA-containing phospholipids comprises at least one PS-DHA phospholipid, PS-EPA phospholipid, PC-DHA phospholipid, or PC-EPA phospholipid.

In another aspect, the phospholipid microbubble further comprises a drug, a fat-soluble compound, an antioxidant, an antibody or a fragment thereof, or a specific ligand is conjugated to the phospholipid microbubble. For example, vitamin A, vitamin D, vitamin E, vitamin K, resveratrol, astaxanthin, or a combination thereof can be conjugated to the phospholipid microbubbles to achieve synergistic or additive effects. With respect to the specific ligand, such specific ligand can bind to an antibody, such as a monoclonal or polyclonal antibody.

In another aspect of the present invention, a method of delivering a prophylactically or therapeutically effective amount of PUFA to an area of disease or injury in a subject, comprising the steps of administering to the subject a plurality of phospholipid microbubbles which comprises a shell comprising a plurality of PUFA-containing phospholipids, and a core of inert gas surrounded by the shell comprising the plurality of PUFA-containing phospholipids; allowing the phospholipid microbubbles to reach the area of disease or injury; and applying ultrasound to the area of disease or injury to explode the phospholipid microbubbles.

In another aspect, the area of disease or injury is the heart.

In another aspect, the plurality of phospholipid microbubbles comprises a micellar form of the phospholipid microbubbles, a liposomal form of phospholipid microbubbles, or a combination thereof.

In another aspect of the present invention, a method of preventing or treating a disease in a subject, comprising the steps of administering to the subject a prophylatically or therapeutic effective amount of a plurality of phospholipid microbubbles which comprises a shell comprising a plurality of PUFA-containing phospholipids, and a core of inert gas surrounded by the shell comprising the plurality of PUFA-containing phospholipids; and applying ultrasound to the phospholipid microbubbles to explode the phospholipid microbubbles in the subject.

In another aspect, the disease can be an inflammatory, autoimmune, neoplastic or degenerative disease. Further, the disease can be lupus erythematosis, multiple sclerosis, rheumatoid arthritis, Crohn's disease, ulcerative colitis, psoriasis, diabetes mellitus, prostate cancer, breast cancer, depression, Alzheimer's disease, myocardial infarction, congestive heart failure, cerebral vascular accidents, or transient ischemic attacks.

In another aspect, the administration is a single intravenous administration of the plurality of phospholipid microbubbles.

In another aspect, the plurality of PUFA-containing phospholipids comprising at least one PS-DHA phospholipid, PS-EPA phospholipid, PC-DHA phospholipid, or PC-EPA phospholipid.

In another aspect, the plurality of phospholipid microbubbles comprises a micellar form of the phospholipid microbubbles, a liposomal form of the phospholipid microbubbles, or a combination thereof.

In another aspect, the administration is a co-administration of a micellar form of the phospholipid microbubbles and a liposomal form of the phospholipid microbubbles.

In another aspect, the co-administration is simultaneous, concurrent or sequential administration of the micellar form of the phospholipid microbubbles and the liposomal form of the phospholipid microbubbles.

Since the phospholipid microbubbles of the present invention can be targeted to areas of disease or injury by using focused ultrasound, a significantly smaller amount of the present invention relative to current delivery methods can be administered intravenously to the subject to achieve diagnostic, prophylactic and/or therapeutic effects. Moreover, due to the characteristics of the inert gas (e.g., a paramagnetic gas) in the microbubble core, the efficacy of prophylactic and/or therapeutic treatment can be further enhanced and monitored by magnetic resonance imaging ("MRI"). This novel formulation strategy promises not only to be disease-specific but also adaptable to treating a wide spectrum of pathological conditions including inflammatory, autoimmune, neoplastic and degenerative diseases.

DEFINITIONS

The term "therapeutically effective amount" as used herein refers to that amount sufficient to treat, manage or ameliorate a disease, disorder or injury in a subject.

The term "prophylactically effective amount" as used herein refers to that amount sufficient to prevent a disease, disorder, or injury in a subject.

The term "subject" as used herein refers to an animal (e.g., a bird, which includes, but not limited to, a chicken, quail or turkey, or a mammal), preferably a mammal which includes, but not limited to, a non-primate (e.g., a cow, pig, horse, sheep, rabbit, guinea pig, goat, rat, cat, dog, and mouse) or a primate (e.g., a monkey, chimpanzee, and human), and more preferably a human. In a preferred embodiment, the subject is a human.

As used herein, the term "antibody" includes, but is not limited to, polyclonal antibodies, monoclonal antibodies, humanized or chimeric antibodies and biologically functional antibody fragments sufficient for binding of the antibody fragment to a protein, See, Harlow & Lane, Antibodies: A Laboratory Manual (Cold Spring Harbor Laboratory Press, Cold Spring Harbor, N.Y., 1988). A "specific ligand" for an antibody is the composition of matter, for example in the blood of a subject, to which an antibody binds with high affinity. Many descriptions of the term "specific ligand" are available to those of skill in the art. See, e.g., van Oss C. J., "Nature of specific ligand-receptor bonds, in particular the antigen-antibody bond." J. Immunoassay 21 (2-3):109-42 (May-August 2000).

BRIEF DESCRIPTION OF THE FIGURES

For the purpose of illustrating the present invention, the drawings reflect a form which is presently preferred; it being understood, however, that the invention is not limited to the precise form shown in the drawings in which.

DETAILED DESCRIPTION OF THE INVENTION

Figure 1:
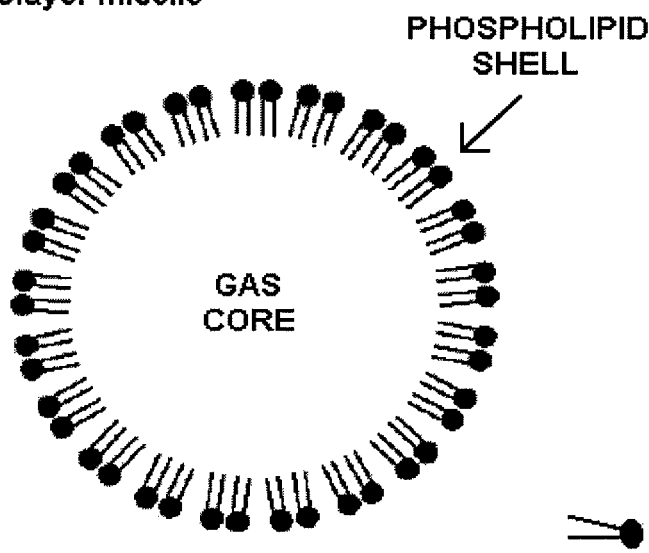
FIG. 1 below shows two exemplary molecular forms of the present invention comprising PUFA-containing phospholipids: (a) a micellar form comprising a monolayer of phospholipids, and (b) a liposomal form comprising a bilayer of phospholipids.
Figure 1:
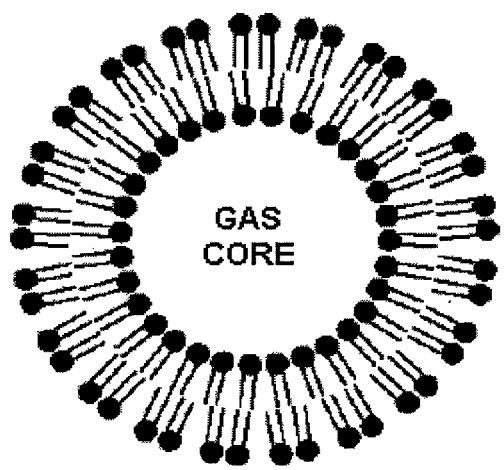

The present invention overcomes many of the existing limitations of current modes of delivery of PUFA (such as omega-3 PUFA) by preferably incorporating them into phospholipid microbubbles and using focused ultrasound to target them to areas of disease or injury.

One of the goals of the present invention is to deliver PUFA (e.g., omega-3 PUFA) as integral components of microbubbles to diseased or injured areas for diagnostic, prophylactic and/or therapeutic purposes. This is achieved by fabricating microbubbles such that they can be delivered efficiently by focused ultrasound and monitored by MRI. The preferred basic structure of these microbubbles is that of a shell which comprises a plurality of phospholipids, and a core of inert gas surrounded by the shell. Each phospholipid within the shell comprises a glycerol backbone to which a polar head group and two non-polar fatty acid tails are linked. The PUFA to be delivered can be linked to the middle (sn-2) position of the glycerol backbone. The polar head group is in the third (sn-3) position while the first (sn-1) position can be either a saturated or unsaturated fatty acid. The types of polar head and non-polar tails can be customized based on an understanding of the underlying pathophysiology of the specific disease or injury to be prevented or treated. Alternatively, the PUFA-containing phospholipids can be derived from a natural source of PUFA, such as those extracted from hill oil.

Prior art gas-encapsulated microbubbles with shells composed either of albumin or lipid have been shown to bind specifically to a variety of inflammatory cells such as neutrophils, monocytes and macrophages and to damaged endothelial cells in vivo. (Lindner J R, Dayton P A, Coggins M P, et al. Noninvasive Imaging of Inflammation by Ultrasound Detection of Phagocytosed Microbubbles. Circulation 2000; 102: 531-8; Villanueva Md F F S, Jankowski Ms R J, Manaugh Bs C, Wagner PhD W R. Albumin Microbubble Adherence to Human Coronary Endothelium: Implications for Assessment of Endothelial Function Using Myocardial Contrast Echocardiography. Journal of the American College of Cardiology 1997; 30:689-93; and Yanagisawa K, Moriyasu F, Miyahara T, Yuki M, Iijima H. Phagocytosis of ultrasound contrast agent microbubbles by Kupffer cells. Ultrasound in Medicine & Biology 2007; 33:318-25). Furthermore, these microbubbles are taken up or phagocytosed into the interior of these cells where they remain acoustically active. Based on these experimental observations, Lindner and his group employed these microbubbles as ultrasound imaging agents to detect areas of inflammation and injury. (Lindner J R, Song J, Xu F, et al. Noninvasive Ultrasound Imaging of Inflammation Using Microbubbles Targeted to Activated Leukocytes. Circulation 2000; 102:2745-50). The microbubbles employed by this group are composed of a mixture of phospholipids containing PC and PS polar head groups linked to stearate acids. Stearate acids are saturated fatty acids that are known to possess proinflammatory properties when they are cleaved and released from their parent phospholipid molecule by cellular enzymes called phospholipases. This fact may account for the success of this imaging technique in detecting inflammation since the stearate acids within these microbubbles actually serve to amplify the inflammatory process. Unfortunately, an unanticipated consequence of these microbubbles is that it tends to exacerbate the underlying inflammatory process that is being imaged, and, thus, explain why this technique has not been adopted clinically for use in humans.

The phospholipid microbubbles of the present invention exploits the known anti-inflammatory effects of omega-3 PUFAs and the proresolving properties of their metabolites, such as resolvins, neuroprotectins and lipoxins. (Serhan C N, Chiang N, Van Dyke T E. Resolving inflammation: dual anti-inflammatory and pro-resolution lipid mediators. Nat Rev Immunol 2008; 8:349-61). Another potential mechanism of benefit relates to the newly discovered anti-inflammatory metabolites formed from peroxidation of omega-3 called neuroprostanes. (Musiek E S, Brooks J D, Joo M, et al. Electrophilic cyclopentenone neuroprostanes are anti-inflammatory mediators formed from the peroxidation of the omega-3 polyunsaturated fatty acid docosahexaenoic acid. J Biol Chem 2008; 283:19927-35). By altering a critical fatty acid component of the lipid shell, these novel formulations can be devoid of the adverse effects of microbubbles made of proinflammatory saturated fatty acids. (Main M L, Goldman J H, Grayburn P A. Ultrasound contrast agents: balancing safety versus efficacy. Expert Opinion on Drug Safety 2009; 8:49-56). Moreover, these new formulations can be used not only for image contrast enhancement but also for treatment purposes. In addition to using focused ultrasound delivery, the target specificity of these microbubbles can be further enhanced by choosing the type of polar head groups appropriate to the disease or injury being prevented or treated. For example, PS is a phospholipid which is an almost universal recognition ligand for phagocytes mediating apoptosis, a cellular mechanism of program cell death that leads to the non-phlogistic healing of inflamed or injured tissues. (Gardai S J, Bratton D L, Ogden C A, Henson P M. Recognition ligands on apoptotic cells: a perspective. J Leukoc Biol 2006; 79:896-903). Thus, the incorporation of PS as polar head groups in the microbubbles' phospholipid shell can enhance microbubble uptake by phagocytic cells within diseased or injured areas. In addition, the phospholipids released from these microbubbles can also compete with endogenous proinflammatory fatty acids (e.g., arachidonic acid) released during the inflammatory process, further promoting its resolution.

Although microbubbles have been used for therapeutic applications such as the delivery of genes, proteins and drugs, they have not been used in the delivery of PUFA as described by the present invention herein. (Bekeredjian R, Grayburn P A, Shohet R V. Use of ultrasound contrast agents for gene or drug delivery in cardiovascular medicine. J Am Coll Cardiol 2005; 45:329-35, and Liu Y, Miyoshi H, Nakamura M. Encapsulated ultrasound microbubbles: Therapeutic application in drug/gene delivery. Journal of Controlled Release 2006; 114:89-99). All existing lipid-based microbubbles in clinical use are composed of saturated fatty acids that may have adverse pro-inflammatory potential. This unrecognized side effect might have accounted for the slight increase in cardiovascular events that prompted their current black box label. (Main M L, Goldman J H, Grayburn P A. Ultrasound contrast agents: balancing safety versus efficacy. Expert Opinion on Drug Safety 2009; 8:49-56). In addition, all existing applications require either the intracellular or intranuclear penetration of the contents of the microbubbles that severely limit the efficiency of delivery. In contrast, the present invention allows the target delivery of fatty acids to the surface of the cell membranes without the need to penetrate into the cytoplasm or nucleus, as it has been shown that omega-3 PUFA exert their acute effects by partitioning into the cell membranes and altering the physiochemical properties of caveolae and of ion-channels within the membrane lipid bilayer. (Weylandt K H, Kang J X, Leaf A. Polyunsaturated fatty acids exert antiarrhythmic actions as free acids rather than in phospholipids. Lipids 1996; 31:977-82; Pound E M, Kang J X, Leaf A. Partitioning of polyunsaturated fatty acids, which prevent cardiac arrhythmias, into phospholipid cell membranes. J Lipid Res 2001; 42:346-51; and Lionetti V, Fittipaldi A, Agostini S, Giacca M, Recchia F A, Picano E. Enhanced Caveolae-Mediated Endocytosis by Diagnostic Ultrasound In Vitro. Ultrasound in Medicine & Biology 2009; 35:136-43). Therefore, the present invention is superior to previous methods in terms of rapidity and efficiency of delivery. The therapeutic effect is expected to occur within seconds and the total duration of administration is anticipated to be not more than one minute rather than more than one hour by currently available methods. The targeted nature of delivery also limits any potential systemic side effects related to treatments using the PUFA-containing microbubbles of the present invention. Moreover, because omega-3 PUFA are natural nutrients, they are devoid of immunogenic potential and can thus be used in repeated administrations. Also, the use of ultrasound for focused delivery of the present invention may not be required since the polar head groups of the present invention can be customized to specifically target areas of inflammation or injury.

The PUFA-containing microbubbles of the present invention can be preferably formulated for intravenous administration as either a bolus or a continuous infusion, and preferably targeted to a specific organ using focused ultrasound. The composition of these microbubbles is customized for a specific disease or injury condition by formulating the type of polar head group and non-polar fatty acid tails of the constituent phospholipids. In addition, other fat-soluble compounds (e.g., antioxidants), the particular type of core gas (e.g., an inert gas, a paramagnetic gas, a perfluorocarbon compound, xenon, hyperpolarized xenon, or other suitable gas that enhances target delivery and/or permits detection and monitoring by MRI) can be chosen to further enhance the diagnostic, prophylactic and/or therapeutic effect.

The PUFA-containing microbubbles can be administered in a micellar form, a liposomal form, or a combination thereof, in varying proportions depending on the specific diagnostic, prophylactic and/or therapeutic aims. The co-administration of the micellar and liposomal forms of the PUFA-containing microbubbles includes simultaneous, concurrent, or sequentially administration of the micellar and liposomal forms to the subject. Simultaneous administration means administration of the micellar and liposomal forms in a single dosage form; concurrent administration means administration of the micellar and liposomal forms at about the same time but in separate dosage forms; and sequential administration means administration of one of the forms, after which the other is administered. Sequential administration can also take the form of simultaneous or concurrent administration(s) of the micellar and liposomal forms, followed by cessation of the simultaneous or concurrent administration(s) and then continued administration of one of the forms alone, or vice versa.

Methods that are well-known to the art can be used to fabricate these microbubbles. For example, a variation of the method as described by Huang et al. can be used. (Huang S-L, McPherson D D, MacDonald R C. A Method to Co-Encapsulate Gas and Drugs in Liposomes for Ultrasound-Controlled Drug Delivery. Ultrasound in Medicine & Biology 2008; 34:1272-80). Briefly, liposomes (or micelles) of the desired composition are prepared from chloroform solutions by combining the appropriate molar amounts of the individual component phospholipids. Alternatively, a natural lipid mixture with the desired phospholipid composition can be obtained by extraction and distillation from natural sources and be used as the starting material. After mixing in a glass vial, the organic solvent is removed by evaporation under argon gas in a 50° C. water bath with constant rotation until a thin film of lipids is formed on the sidewall of the vial. The lipid film is then placed under high vacuum for 5 hours for complete removal of the solvent. The dried lipid film is hydrated with 0.32 mol/L mannitol. This is followed by sonication using a sonoporation unit with 1-Mhz frequency for 5 min in a water bath. The mixture is then transferred to a new glass vial and capped with an open screw cap containing Teflon-covered silicon rubber septa. The desired gas (e.g., octafluorocyclobutane) is then introduced into this vial by injection using a syringe through its cap. The gas and liposome dispersion is then pressurized to a supra-atmospheric level ranging from 3 to 9 atms depending on the composition of the desired lipid dispersion. This pressurized system is incubated for 30 minutes at room temperature and then frozen by cooling to −78° C. in dry ice for at least another 30 minutes. After this incubation, the pressure is released by unscrewing the cap immediately upon its removal from dry ice. The depressurized frozen liposomes are then thawed by exposure to room air. The final product will be ready for use when its temperature reaches at least 24° C. (usually after 10 minutes). Additional compounds such as free fatty acids or other protein ligands can be loaded at various points along this procedure (e.g., mixing with mannitol at the hydrating step).

Due to the versatility of these phospholipid microbubbles and the wide-ranging health effects of omega-3 PUFA, the present invention has multiple potential therapeutic applications. In an aspect of the present invention, phospholipid microbubbles are custom-formulated for use in the treatment of acute myocardial infarction and the prevention of its arrhythmic complications. For this application, phospholipid microbubbles having a phospholipid shell comprising a mixture of PS and PC head groups linked to a non-polar fatty acid tail mixture of omega-3 PUFA including EPA and DHA are specifically fashioned. These phospholipid microbubbles containing a mixture of PS-DHA, PS-EPA, PC-DHA, PC-EPA can be given to a patient before, during and/or after a myocardial infarction. The beneficial effects of omega-3 PUFA in this life-threatening condition are myriad and include the reduction of infarct size, prevention of atrial and ventricular arrhythmias, decrease in reperfusion injury, promotion of the healing process, prevention of sudden death, and ultimately translating to the prolongation of survival. (Jacobson T A. Secondary Prevention of Coronary Artery Disease with Omega-3 Fatty Acids. The American Journal of Cardiology 2006; 98:61-70, and Jung U J, Torrejon C, Tighe A P, Deckelbaum R J. n-3 Fatty acids and cardiovascular disease: mechanisms underlying beneficial effects. Am J Clin Nutr 2008; 87:2003S-9S). In addition, omega-3 PUFA can exert anti-atherosclerotic, anti-inflammatory and anti-thrombotic effects on the ruptured culprit coronary plaque that precipitated the myocardial infarction. (Robinson J G, Stone N J. Antiatherosclerotic and antithrombotic effects of omega-3 fatty acids. Am J Cardiol 2006; 98:39i-49i). Therefore, these phospholipid microbubbles can be used to stabilize inflamed or eroded atherosclerotic plaque during an acute coronary event or during a transient cerebral ischemia or infarction. (Thies F, Garry J M C, Yaqoob P, et al. Association of n-3 polyunsaturated fatty acids with stability of atherosclerotic plaques: a randomised controlled trial. The Lancet 2003; 361:477-85).

In Vivo Experiments

One of the aforementioned effects associated with the present invention was tested in a canine model of myocardial infarction. Specifically, phospholipid microbubbles containing omega-3 PUFA were custom-formulated to test for their purported anti-arrhythmic effects in this established post-infarct animal model. The omega-3 PUFA-containing phospholipids used in this formulation were derived from a natural marine source called Antarctic krill (*Euphausia superba*). The omega-3 PUFA-containing phospholipids extracted from Antarctic krill comprise predominantly of PC and PS forms of DHA and EPA. For microbubbles preparation, 30 milligram of these omega-3 PUFA-containing phospholipids was mixed with 1 mg of poly(ethyleneglycol) stearate (Sigma Chemical Co) and dissolved in normal saline (0.9%) to a final volume of 1 milliliter. This dispersion was then transferred to a glass vial and sonicated under room air for 40 seconds. The final concentration of microbubbles generated by this method was estimated to be $10^7$/ml. One milliliter of this freshly prepared microbubbles solution was used to test for its ability to terminate ventricular tachycardia, a life-threatening arrhythmia that frequently develops after a myocardial infarction.

Figure 2:
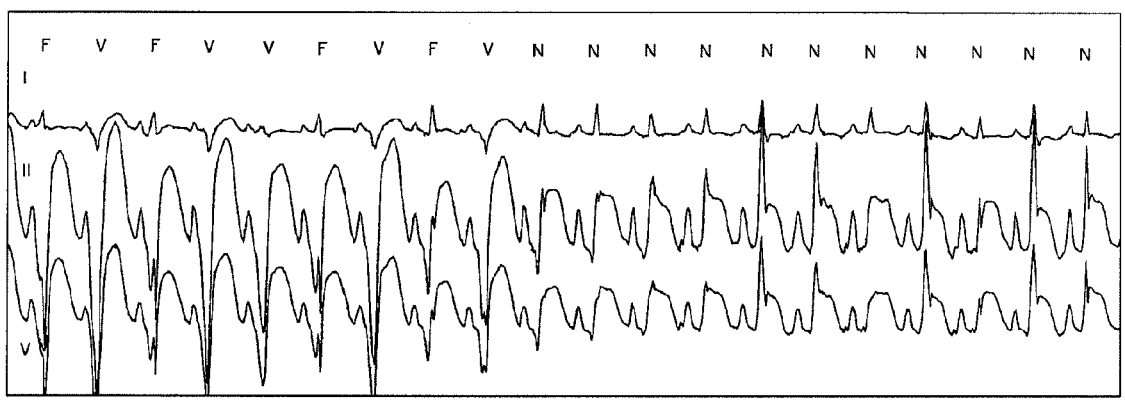
FIG. 2 below shows anti-arrhythmic effects of omega-3 PUFA-containing microbubbles in a dog with myocardial infarction. Specifically, three representative leads (I, II and V) from a surface electrocardiographic recording of a dog with myocardial infarction demonstrating conversion from ventricular tachycardia to normal sinus rhythm. Within a few seconds after microbubbles administration and application of transthoracic ultrasound over the region of infarct, abnormal ventricular beats (V) were replaced by normal sinus beats (N). Fusion beats (F) formed from a combination of V and N beats were observed during the early part of the transition.

To induce ventricular tachycardia, a myocardial infarction was produced in a mongrel dog by ligation of the proximal left anterior descending coronary artery under anesthesia with pentobarbital sodium (20 to 25 mg/kg IV). The successful creation of myocardial infarction was ascertained by direct visualization of an anterior wall motion abnormality by echocardiography. The cardiac rhythm was continuously monitored and recorded via a five-lead surface electrocardiogram using a telemetry unit throughout the experiment. Ventricular tachycardia developed at 15 minutes into the experiment, upon which a 1-ml bolus of microbubbles containing omega-3 PUFA was immediately injected via an intravenous femoral catheter together with simultaneous application of ultrasound over the region of infarction. Within a few seconds after microbubbles injection, the abnormal ventricular tachycardia reverted back to normal sinus rhythm. This dramatic pharmacologic conversion was recorded and is shown in FIG. 2. After microbubbles administration, the dog remained in sinus rhythm without further arrhythmias for another hour.

In another experiment, an experimental dog developed an anterior wall myocardial infarction after ligation of the left anterior descending coronary artery. About 30 minutes after the infarction, the dog developed ventricular fibrillation. A 0.5 ml bolus of microbubbles containing omega-3 PUFA was administered intravenously which immediately restored the abnormal rhythm back to normal sinus rhythm for 1 beat. Although transient, this unusual event provided evidence of a positive anti-arrhythmic effect associated with the administration of the PUFA-containing microbubbles in the dog. However, the dog's rhythm then degenerated back into ventricular fibrillation. Because of hemodynamic instability, electrical defibrillation was performed twice in rapid sequence without effect. Another 0.5 ml bolus of PUFA-containing microbubbles was injected and electrical defibrillation was subsequently attempted, which then successfully restored sinus rhythm back to normal. The results of this experiment shows that PUFA-containing microbubbles can be useful in lowering the electrical threshold needed for successful defibrillation.

In another experiment, an experimental dog developed ventricular flutter and fibrillation after an extensive myocardial infarction involving a large territory of the anterior wall as visualized by echocardiography after coronary ligation. Intravenous injection of a 1 ml bolus of microbubbles containing omega-3 PUFA failed to restore sinus rhythm. Subsequent electrical defibrillation in 3 consecutive attempts was also unsuccessful. As a last measure, direct manual massage of the exposed heart also failed to restore the rhythm. Finally, another 1 ml bolus was injected after which manual massage successfully restored the rhythm back to normal. Because of the extensive nature of the infarction, the dog suffered from severe circulatory failure which prevented effective intravenous delivery of the PUFA-containing microbubbles. In this severe circulatory failure scenario, a larger dose combined with direct manual massage made it possible for the PUFA-containing microbubbles to exert its anti-arrhythmic effect.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. A method of delivering a therapeutically effective amount of PUFA to a heart of a subject having myocardial infarction, comprising the steps of:
    administering intravenously to the subject a plurality of liposomal phospholipid microbubbles each comprising:
        a shell comprising:
            a plurality a first phospholipids each having a first phosphatidylserine (PS) headgroup and a PUFA esterified to an sn-2 position of the first phospholipid, wherein the first PUFA is one of eicosapentaenoic acid (EPA) and docosahexaenoic acid (DHA),
            a plurality of second phospholipids each having a phosphatidylcholine (PC) headgroup and a second PUFA esterified to an sn-2 position of the second phospholipid, wherein the second PUFA is one of eicosapentaenoic acid (EPA) and docosahexaenoic acid (DHA), and
            a core of inert gas surrounded by the shell comprising the plurality of PUFA-containing phospholipids;
    allowing the phospholipid microbubbles to reach the heart; and
    applying ultrasound to the heart to explode the phospholipid microbubbles.

2. A method of treating myocardial infarction in a subject, comprising the steps of:
    administering intravenously to the subject a therapeutically effective amount of a plurality of liposomal phospholipid microbubbles each comprising:
        a shell comprising:
            a plurality a first phospholipids each having a first phosphatidylserine (PS) headgroup and a PUFA esterified to an sn-2 position of the first phospholipid, wherein the first PUFA is one of eicosapentaenoic acid (EPA) and docosahexaenoic acid (DHA),
            a plurality of second phospholipids each having a phosphatidylcholine (PC) headgroup and a second PUFA esterified to an sn-2 position of the second phospholipid, wherein the second PUFA is one of eicosapentaenoic acid (EPA) and docosahexaenoic acid (DHA), and
            a core of inert gas surrounded by the shell comprising said plurality of PUFA-containing phospholipids; and
        applying ultrasound to the phospholipid microbubbles to explode the phospholipid microbubbles in the heart of the subject.

3. The method of claim 2, wherein the administration is a single intravenous administration of the plurality of phospholipid microbubbles.

4. The method of claim 3, wherein the plurality of first phospholipids and plurality of second phospholipids each further comprise a saturated or monosaturated fatty acid in the sn-1 position.

* * * * *